United States Patent [19]

McLean

[11] Patent Number: 4,833,807

[45] Date of Patent: May 30, 1989

[54] LOCKABLE SECURITY IDENTIFICATION WRISTSTRAP

[75] Inventor: Donald A. McLean, Vancouver, Canada

[73] Assignee: Panorama Plastics Ltd., Vancouver, Canada

[21] Appl. No.: 128,807

[22] Filed: Dec. 4, 1987

[51] Int. Cl.$^4$ .................................... A61B 5/00

[52] U.S. Cl. .................................... 40/633; 24/17 AP; 292/325

[58] Field of Search .................... 40/21 C, 304, 633; 24/16 PB, 265 EC, 17 A, 17 AP, 20 EE; 292/320, 321, 325, 318

[56] References Cited

U.S. PATENT DOCUMENTS

| | | | |
|---|---|---|---|
| 538,192 | 4/1895 | Foote | 292/318 |
| 908,186 | 12/1908 | Wing | 292/321 |
| 1,026,701 | 5/1912 | Reid | 292/318 |
| 1,176,181 | 3/1916 | Thomas | 40/304 |
| 2,103,292 | 12/1937 | Leach | 40/304 |
| 2,337,729 | 12/1943 | Ashton | 40/304 |
| 2,341,608 | 2/1944 | Gey | 40/304 |
| 2,426,731 | 9/1947 | Elliott | 24/16 PB |
| 2,954,621 | 10/1960 | Mosher, Jr. et al. | 40/19 |
| 3,112,496 | 12/1963 | Dritz | 24/17 AP |
| 3,149,869 | 9/1964 | Chamberlin | 292/320 |
| 3,556,575 | 1/1971 | Farkas | 292/307 R |
| 3,954,294 | 5/1976 | Iwamoto et al. | 292/318 |
| 4,154,011 | 5/1979 | Rakestraw et al. | 40/21 C |
| 4,272,900 | 6/1981 | MacLarty et al. | 40/21 C |
| 4,377,887 | 3/1983 | Valestin | 24/16 PB |
| 4,501,049 | 2/1985 | Adamson | 24/30.5 P |
| 4,506,415 | 3/1985 | Swift | 24/16 PB |
| 4,609,218 | 9/1986 | Chevillard et al. | 292/320 |
| 4,680,834 | 7/1987 | Andre et al. | 24/17 AP |

*Primary Examiner*—Gene Mancene
*Assistant Examiner*—Cary E. Stone
*Attorney, Agent, or Firm*—Marger & Johnson

[57] ABSTRACT

This invention pertains to a novel waterproof locking wriststrap which is useful for personnel identification and admission control to amusement parks, waterslide parks, and other admission charge crowd related activities. A wriststrap comprising: (a) a strap which has at one end thereof one or more protrusions and at the opposite end one or more grooves, which protrusion and groove are adapted to mate with one another in an interlocking relationship, the end with the groove having therein at least one opening; and (b) a lock which can be moved into place over the protrusion when it mates with the groove, the lock having therein tangs which are adapted to extend into the opening of the strap.

8 Claims, 2 Drawing Sheets

LOCKABLE SECURITY IDENTIFICATION WRISTSTRAP

FIELD OF THE INVENTION

This invention pertains to a novel waterproof locking wriststrap which is useful for personnel identification and admission control to amusement parks, waterslide parks, and other admission charge crowd related activities.

BACKGROUND OF THE INVENTION

Admission control at large crowd related events which have an admission charge, such as amusement parks, water slide parks, concerts, and the like, has been a longstanding problem. In the past, in an effort to exercise control, persons admitted to an event have been wrist or hand stamped with a specific ink symbol, when the admission charge is paid, in order to provide notice to scrutineers that admission has been paid, and also to permit the person to leave and return to the event without paying double admission. However, unscrupulous individuals intent on avoiding payment of the admission charge have devised ways to duplicate the stamp or transfer stamped impressions from the hand of one person to the hand of another person. Moreover such stamps are not satisfactory if the event involves swimming, because the ink symbol washes off or fades. Waterproof inks are not acceptable because they can not be washed off after the event. Lastly, ink stamps can often smudge, which defeats the purpose of being able to identify a clear impression on the hand or wrist of a patron.

More recently, color coded plastic wriststraps which are disposed of after the event, have become a common means of paid admission identification. However, such straps are not foolproof and are subject to a new set of shortcomings. Many can be stretched and thus transferred from the wrist of one person to another. Also, the locks on such wriststraps can usually be picked by using a sharp pin or other thin object to release the internal locking mechanism.

It is common for identification wriststraps to be made of laminated vinyl and held together by a metal or plastic rivet, or for the wriststrap to be a plastic sheet held together with glue from a piece of transfer tape. These designs are unreliable because the straps can be stretched and slid off the wrist, or the vinyl can be pulled over the plastic or metal rivet. In straps which use transfer glue, the transfer tape glue takes too long to set and can be peeled back immediately, or even later, with a sharp instrument such as the flat edge of a pen knife. It is important in those cases where large numbers of people must be passed through turnstiles, and the like, as rapidly as possible that the identification system be fast as well as foolproof. Transfer glue-type straps are not satisfactory for this purpose. It is evident that these designs are not tamper resistant, and as a consequence, the admission paying patron can transfer the wriststrap to a non-paying individual without detection.

Strings and metal clips have also been used but they are not satisfactory because the metal clip sometimes cuts into the wrist of the wearer and this creates a legal liability problem for the owner or operator of the event.

The applicant is aware of a number of patents which disclose various designs of wriststraps and fastening straps. These are listed below.

U.S. Pat. No. 2,103,292, H. Leach, Dec. 28, 1937, entitled "Seal".

U.S. Pat. No. 2,954,621, W. W. Mosher, Jr., et al., Oct. 4, 1960, entitled "Adjustable Bracelet for Identification Purposes".

U.S. Pat. No. 3,149,869, C. R. Chamberlin, Sept. 22, 1964, entitled "One-Time Use Plastic Lock".

U.S. Pat. No. 3,556,575, P. Farkas, Jan. 19, 1971, entitled "Tamperproof Seal".

U.S. Pat. No. 3,954,294, Iwamoto et al., May 4, 1976, entitled "Plastic Sealing Device".

U.S. Pat. No. 4,154,011, Rakestraw et al., May 15, 1979, entitled "Personalized Identification Band".

U.S. Pat. No. 4,272,900, MacLarty et al., June 16, 1981 entitled "Identity Band".

U.S. Pat. No. 4,501,049, Adamson, Feb. 26, 1985, entitled "Disposable One-Piece Security Sealing Device".

U.S. Pat. No. 4,506,415, Switt, Mar. 26, 1985, entitled "Security Seal and Tag Holder".

U.S. Pat. No. 4,609,218, Chevillard et al., Sept. 2, 1986, entitled "Plastic Seal".

Of these patents, two are considered to be relevant to the invention that is disclosed and claimed herein. Mosher et al. discloses an adjustable disposable identification bracelet which is adapted to be utilized in single use situations. Among other things, Mosher discloses a complicated self-locking fastener which, once engaged on the strap, cannot be dislodged. The strap is removed by cutting the strap. The strap is made up of a number of separate parts and is relatively expensive to manufacture.

MacLarty discloses an identity band which comprises an elongate strap and a latch portion which forms a slot through which the strap is pushed to form the band into a loop. The strap has a series of apertures therein providing a series of transverse stop surfaces alternating with a series of transverse camming surfaces. Within the slot there is a latching element. As the strap is pushed through the slot to form the loop, the camming surfaces in turn cam the latching element out of the path of the strap to permit passage thereof through the slot. The stop surfaces are arranged so that, if an attempt is made to pull the strap in the opposite direction through the slot one of them engages with the latching element to prevent such movement of the strap. Both the stop surfaces and the camming surfaces meet the upper and lower faces of the strap portion at angles other than right angles. The latch element is wedge-like and mounted at its thicker end. The band is formed so that it can carry information identifying the person wearing the band.

A problem with the MacLarty identity band is that the latch locks in only one direction and thus the strap can continue to be pulled through the latch, thus choking off the circulation to the hand if the strap becomes caught on some unyielding object. Also, the latch disclosed by MacLarty can be tampered with or unlocked by inserting a sharp pin or other suitable object into the latch to release the locking member.

SUMMARY OF THE INVENTION

A wriststrap comprising (a) wrist encircling means which has at one end thereof a protrusion and at the opposite end a groove, which protrusion and groove are adapted to mate with one another in an interlocking relationship, said end with the groove having therein at least one opening; and (b) locking means which can be moved into place over the protrusion when it mates with the groove, the locking means having therein projection means which is adapted to extend into the opening of the wrist encircling means.

In the wriststrap, the wrist encircling means may have a plurality of protrusions and a plurality of grooves. The locking means may have two projections, and the wrist encircling means may have two corresponding openings.

In the wriststrap as defined, the wrist encircling means may have formed thereon an abutment against which the locking mechanism abuts when moved into place over the mating protrusion and groove. The internal width of the locking means may be wider at one end than the other. The narrower internal width of the locking means may be slightly larger than the external width of the wrist encircling means. In the wriststrap, the end of the wrist encircling means having the openings therein may have along each side a slide rail, the locking means fitting over the slide rails when the locing means is in a position where the pair of protrusions in the locking means extends into the pair of openings in the wrist encircling means.

DRAWINGS

In the drawings which illustrate a specific embodiment of the invention, but which should not be construed as restricting the spirit or scope of the invention in any way:

Figure 5:
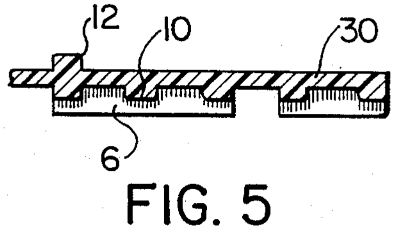
FIG. 5 illustrates an enlarged side section view of the slide mechanism.
Figure 6:
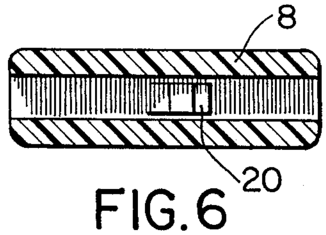
Figure 5A:
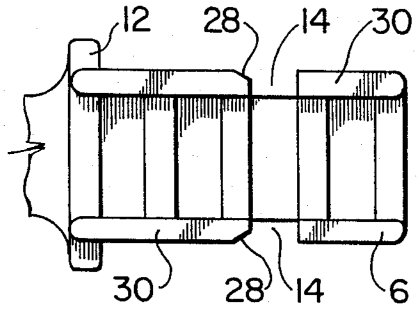

FIG. 5*a* illustrates an enlarged top view of the slide mechanism;

FIG. 6 illustrates an enlarged side section view of the lock; and

Figure 6A:
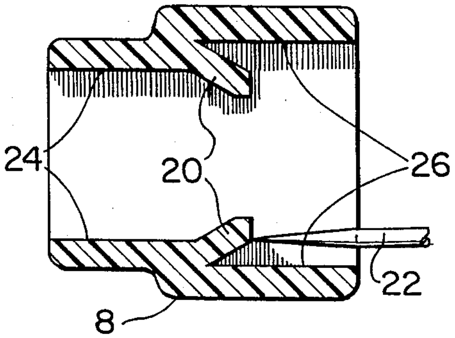

FIG. 6*a* illustrates an enlarged top section view of the lock.

DETAILED DESCRIPTION OF A SPECIFIC EMBODIMENT OF THE INVENTION

In this invention, the strap and slide mechanism are constructed as an integral piece of injection molded plastic. The lock mechanism is separate and constructed in a configuration that is integral to the design of the strap. The strap is designed to be of a sufficiently heavy guage that it is unstretchable, even if submersed in hot water such as is found in whirlpool baths. The lock is designed specifically to permit the strap to be adjusted to the appropriate length around the wrist and then lock securely about the strap and slide mechanism. The lock is designed to be tamperproof. The combination of the unstretchable nature of the strap and the tamperproof lock mechanism make it impossible to transfer the strap from one wrist to another.

In operation, the locking mechanism is slid into place after the strap has been placed about the wrist and adjusted to snug size. The lock is securely held in place by a combination of two tangs which fit into grooves in the slide mechanism. These tangs cannot be pried open again. The meshing of the ridges and grooves of the strap and the slide mechanism add to the security. The combination of all these features results in a strap that is unstretchable, tamperproof, and as a result is non-transferable from one person to another.

Figure 1:
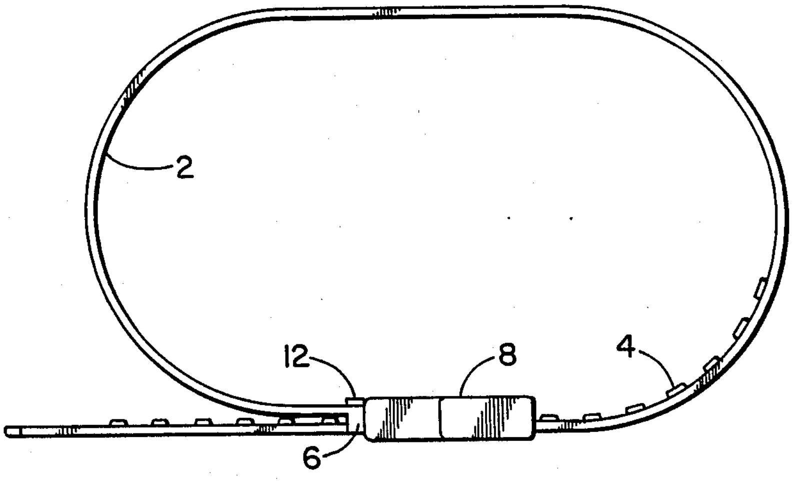
FIG. 1 illustrates a side view of the wriststrap in a looped configuration with the lock in place over adjacent straps.

Referring to the drawings, FIG. 1 illustrates a side view of the wriststrap 2 shown in a looped configuration and locked by means of lock 8. The wriststrap 2 has along the interior face thereof a series of equally spaced ridges 4, which are located proximate to the free end of the strap 2, that is, remote from the end of the wriststrap 2 which has slide mechanism 6 attached to it. As seen in FIG. 1, a lock 8 has been moved into position over slide mechanism 6. The lock 8 has been moved to a position so that it abuts lock stop 12, which is formed as part of slide mechanism 6.

Figure 2:
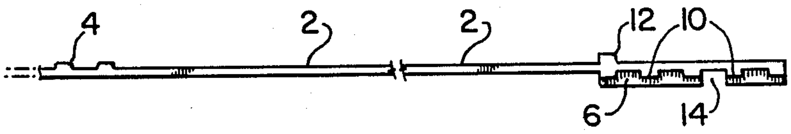
FIG. 2 illustrates a side view of the wriststrap in extended position without the lock.

FIG. 2 illustrates in side elevation view the wriststrap 2, with spaced ridges 4 formed at one end of the strap, and projecting upwardly (as seen in FIG. 2) and at the opposite end of the strap 2, slide mechanism 6. As seen in FIG. 2, slide mechanism 6 has formed therein a series of equally spaced apart grooves 10, which are formed to receive ridges 4, of the opposite end of the strap, when the strap is looped in a circular or oval manner as illustrated in FIG. 1. A tang receptacle 14 is also illustrated in the lock mechanism 6, as illustrated in FIG. 2.

Figure 3:
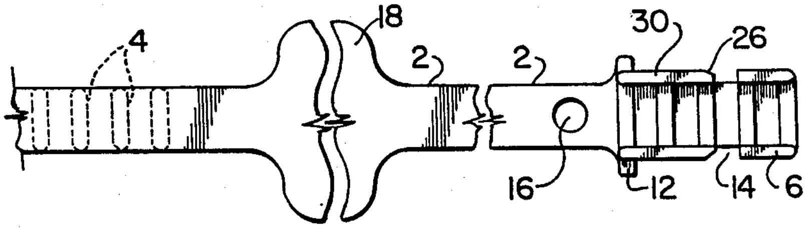
FIG. 3 illustrates a top view of the wriststrap without the lock.

FIG. 3 illustrates a top view of the strap 2. Spaced ridges 4 are illustrated by means of dotted lines. At the end of the strap 2 opposite ridges 4, it can be seen that the slide mechanism 6 is constructed so that it is connected to strap 2 at the end opposite ridges 4. Lock stops 12, project from either side of the strap 2. A pair of tang receptacles 14 are shown formed in the slide mechanism 6. The slide mechanism 6 also has a pair of longitudinal extending side rails 30, which are designed, and spaced apart a sufficient distance that they comfortably receive the sides of the opposite end of the strap 2, which has the spaced ridges 4 there along. In this way, a snug fit is formed between the strap which has the ridges 4 thereon, and the slide mechanism 6, as defined by the pair of side rails 30, when the two ends of the strap are adjoined. A hole 16 is formed in the strap 2 at a point proximate to the slide mechanism 6. This hole 16 is formed in the strap to assist in permitting the strap 2 to be broken, when any person wearing the strap 2 wishes to remove the strap 2 from his or her wrist. FIG. 3 also illustrates an identification plate 18, which can be used to carry some sort of message, identification symbol or code, as may be required by the person or corporation employing the identification straps.

Figure 4:
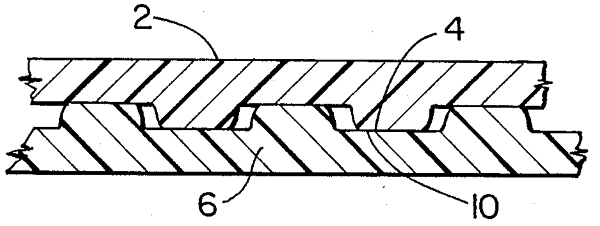
FIG. 4 illustrates an enlarged side view of two adjacent straps juxtaposed with one another.

FIG. 4 illustrates in detailed side elevation view, the manner in which the spaced ridges 4 of strap 2 fit or mate with spaced grooves 10 of slide mechanism 6 when the strap 2 is looped, as shown in FIG. 1. As can be seen, the width of the grooves 10 are slightly greater than the width of the ridges 4, thus permitting a certain amount of "play" between the ridges 4 and the grooves 10. This promotes rapid and ready fitting between the ridges 4 of strap 2 and the slide mechanism 6, when the straps are being used at an admission event.

FIGS. 5 and 5*a* illustrate respectively detailed side and plan views of the construction of slide mechanism 6. As seen in FIG. 5, slide mechanism 6 has formed therein a series of spaced apart grooves 10, as explained previously. Lock stop 12 is also illustrated in FIG. 5. FIG. 5*a* illustrates in plan view the location of the pair of tang receptacles 14, as formed in the pair of side rails 30. One side of the pair of tang receptacles 14 has respective bevelled edges 28. These bevelled edges 28 are formed to promote comfortable reception of the pair of locking tangs 20, (see FIG. *6a*) when lock 8 is moved into position over slide mechanism 6 and strap 2 (as shown in FIG. 4).

FIGS. 6 and *6a* illustrate in detailed side section and plan section view respectively, the construction of the lock 8. As seen particularly in FIG. *6a*, the lock 8 is formed so that it is hollow and has protruding inwardly at an angle from the respective sides thereof a pair of locking tangs 20. These tangs 20 are angled approximately 30° with the center line of the locking mechanisms 8 to promote ready slideability of the lock 8 over the slide mechanism 6. Also, the inner width 24 of the head of lock 8 is sized so that it corresponds closely with the exterior width of the pair of side rails 30 of slide mechanism 6. On the other hand, the inner width 26 of the tail end of lock 8 is sized so that it is wider than the exterior width of the pair of side rails 30 of slide mechanism 6. A pin or needle 22 is also illustrated in FIG. 6, and will be discussed in more detail below.

The wriststrap 2 is secured above the wrist of a person to be identified by first looping the strap 2 around the wrist of the person in a circular or oval manner as illustrated in FIG. 1. It is preferable that the ridges 4 project inwardly toward the wrist of the wearer. The wriststrap 2 is wrapped so that it is snug about the wrist of the person to be identified, and cannot be slipped over the hand of that person. Once the proper fit for the wriststrap 2 has been determined, and the ridges 4 are closely aligned in respective grooves 10 of slide mechanism 6, in other words, the grooves 10 of slide mechanism 6 meet with the corresponding ridges 4 of wriststrap 2, the lock 8 is then slid into place so that it encloses both the strap 2, and the slid mechanism 6. The lock 8 is slid to a position where it abuts lock stop 12. At that point, the inwardly projecting tangs 20 correspond with receptacles 14 and thus spring inwardly so that they project into the pair of tang receptacles 14. At that point, the lock 8 cannot be moved in either direction relative to slide mechanism 6. The lock stop 12 prevents the lock 8 from being moved along the wrist strap 2 in the direction of end of the wriststrap 2 bearing the ridges 4. On the other hand, by means of locking tangs 20, which have extended into the tang receptacles 14, the lock 8 cannot be moved in the opposite direction off of slide mechanism 6. Moreover, the lock 8 is tamperproof because a pin or needle, such as pin 22 illustrated in FIG. *6a*, cannot be used to push the tangs 20 out of place. As seen in FIG. *6a*, any force exerted on tang 20 by a pin 22 simply urges the tang 20 further into receptacle 14. Moreover, because of the angle of tangs 20, they cannot be pulled free, particularly both of them. From the other end of lock 8, the inner width 24 of the head of lock 8 closely mates with the outer width of the pair of rails 30 of slide mechanism 6. Thus, it is not possible to insert a pin 22 into that end of lock 8 in order to attempt to push tangs 20 out of the receptacles 14. The only way that the wrist strap 2 can be removed from the wrist of the person that has been identified is to break the strap, either at hole 16, or by means of scissors or knife.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

I claim:

1. A lockable wriststrap comprising:

(a) wrist encircling means which has at one end thereof a protrusion and at the opposite end a groove, which protrusion and groove are adapted to mate with one another in an interlocking relationship, said end with the groove having therein an opening; and (b) locking means which can be moved into place over the protrusion when it mates with the groove, the locking means having therein projection means which is adapted to extend into the opening of the wrist encircling means;

the wrist encircling means having formed thereon an abutment against which the locking means abuts when moved into place over the mating protrusion and groove.

2. A wriststrap as defined in claim 1 wherein the wrist encircling means has a plurality of protrusions and a plurality of grooves

3. A wriststrap as defined in claim 2 wherein the locking means has two projections, and the wrist encircling means has two corresponding openings.

4. A wriststrap as defined in claim 3 wherein the internal width of the locking means is wider at one end than the other.

5. A wriststrap as defined in claim 4 wherein the narrower internal width of the locking means is slightly larger than the external width of the wrist encircling means.

6. A wriststrap as defined in claim 4 wherein the end of the wrist encircling means having the openings therein has along each side a slide rail, the locking means fitting over the slide rails when the locking means is in a position where the pair of protrusions in the locking means extends into the pair of openings in the wrist encircling means.

7. A method of identifying an individual with a one-time lockable non-relockable wriststrap, the method comprising:

encircling one wrist of the individual with a wriststrap so that opposite, first and second end portions of the wriststrap overlap, the wriststrap having a protrusion in the first end portion and a groove in second end portion, the first end portion including an opening and an abutment spaced apart therealong;

mating the protrusion and groove with one another in interlocking relationship;

sliding a locking means along the overlapping end portions of the wriststrap into position over the protrusion when mated with the groove, the locking means having a projection positioned to register in the opening;

abutting the locking means against the abutment in the first end portion of the wriststrap when the locking means is moved into position over the mating protrusion and groove; and inter-engaging the projection of the locking means into the opening of the wriststrap when the locking means is moved into position over the protrusion.

8. A method according to claim 7 including providing a plurality of said grooves and protrusions; and fitting the wriststrap to the individual's wrist so that the strap cannot be removed by sliding the wriststrap over the individual's hand.

* * * * *